(12) United States Patent
Bull et al.

(10) Patent No.: US 12,240,801 B2
(45) Date of Patent: Mar. 4, 2025

(54) METHOD OF SYNTHESIS AND PURIFICATION OF CITRULLINE

(71) Applicant: Asklepion Pharmaceuticals, LLC, Baltimore, MD (US)

(72) Inventors: James Alan Bull, Freiburg (DE); Holger Christian Fischer, Freiburg (DE); Karl Juergen Kaiser, Freiburg (DE); Bette Monnot-Chase, Baltimore, MD (US)

(73) Assignee: ASKLEPION PHARMACEUTICALS, LLC, Baltimore, MD (US)

( * ) Notice: Subject to any disclaimer, the term of this patent is extended or adjusted under 35 U.S.C. 154(b) by 633 days.

(21) Appl. No.: 17/616,394

(22) PCT Filed: Jun. 5, 2020

(86) PCT No.: PCT/US2020/036468
§ 371 (c)(1),
(2) Date: Dec. 3, 2021

(87) PCT Pub. No.: WO2020/247853
PCT Pub. Date: Dec. 10, 2020

(65) Prior Publication Data
US 2022/0227702 A1    Jul. 21, 2022

Related U.S. Application Data

(60) Provisional application No. 62/857,612, filed on Jun. 5, 2019.

(51) Int. Cl.
C07C 273/16    (2006.01)
A61K 9/00    (2006.01)
C07C 273/18    (2006.01)

(52) U.S. Cl.
CPC ...... *C07C 273/1809* (2013.01); *A61K 9/0029* (2013.01); *C07C 273/16* (2013.01)

(58) Field of Classification Search
None
See application file for complete search history.

(56) References Cited

U.S. PATENT DOCUMENTS

| 4,948,594 A | 8/1990 | Abdel-Monem et al. |
| 7,129,375 B2 | 10/2006 | Abdel-Monem et al. |
| 2012/0315372 A1 | 12/2012 | Stark |

FOREIGN PATENT DOCUMENTS

| JP | S48-040337 B1 | 11/1973 |
| WO | 2005082042 A2 | 9/2005 |
| WO | 2012/165356 A1 | 12/2012 |

OTHER PUBLICATIONS

Jia et al. (J. Chem.Soc. Pak., 2012 (vol. 34), No. 2, p. 451) (Year: 2012).*

(Continued)

*Primary Examiner* — Sudhakar Katakam
*Assistant Examiner* — Jennifer C Sawyer
(74) *Attorney, Agent, or Firm* — ArentFox Schiff LLP

(57) ABSTRACT

This invention provides for synthesis of citrulline from a transition metal complex of ornithine using cyanate to derivatize the terminal amino group of ornithine. The invention also provides improved methods for purification of citrulline produced by reaction of cyanate with ornithine via the steps of reprecipitation of copper complex of citrulline, removal of the complexing metal by sulfide precipitation, activated carbon adsorption and antisolvent crystallization.

4 Claims, 6 Drawing Sheets

(56) References Cited

OTHER PUBLICATIONS

Smith L.H Jr., "A Simple Synthesis of Isotopic Citrulline and Two of its Homologs", Journal of American Chemical Society, 1955, vol. 77, Aug. 10, 1955, pp. 6691-6692.

Kurtz, A. C., "A simple synthesis of dl-citrulline," Journal of Biological Chemistry, 1938, vol. 122, No. 2, pp. 477-484.

Kurtz, A. C., "Use of copper (II) ion in masking a-amino groups of amino acids," Journal of Biological Chemistry, 1949, vol. 180, No. 3, pp. 1253-1267.

* cited by examiner

METHOD OF SYNTHESIS AND PURIFICATION OF CITRULLINE

CROSS-REFERENCE TO RELATED APPLICATIONS

This application is a 35 U.S.C. § 371 National Phase of PCT Application No. PCT/US2020/036468, filed Jun. 5, 2020, which claims priority to U.S. Provisional Application No. 62/857,612, filed Jun. 5, 2019, the disclosures of each of which are incorporated herein by reference in their entirety.

FIELD OF THE INVENTION

This invention provides for synthesis of citrulline from a transition metal complex of ornithine using cyanate to derivatize the terminal amino group of ornithine. The invention also provides improved methods for purification of citrulline produced by reaction of cyanate with ornithine via the steps of reprecipitation of copper complex of citrulline, removal of the complexing metal by sulfide precipitation, activated carbon adsorption and antisolvent crystallization.

BACKGROUND

Ornithine is an alpha amino acid with a terminal amino group opposite the alpha carbon. Citrulline is an alpha amino acid with a terminal carbamido group in the same position as the terminal amino group of ornithine. Dr. A. Kurtz described synthesis of racemic citrulline from racemic ornithine in 1938 (J. Biol. Chem., 122:477-484), and that disclosure was followed up by synthesis of optically active /-citrulline from /-ornithine in 1949 (J. Biol. Chem., 180: 1253-1267). Optical activity was preserved by complexing the starting material (/-ornithine) in a transition metal complex via the alpha amino and carboxyl groups, then reacting the terminal amino group with urea to from a carbamido derivative (see FIG. 1). Kurth 1949 describes numerous other syntheses, all depending on the transition metal complex to preserve the alpha amino acid character of the starting compound while derivatizing other parts of the molecule. An example of this synthesis is described in Example 1 below.

SUMMARY OF THE INVENTION

This invention provides an improved method for adding a terminal carbamide group to an alpha amino acid by taking an alpha-amino acid having a terminal amine that has been complexed with copper and exposing it to an excess of cyanate in aqueous solution. The cyanate reacts with the terminal amine to form a carbamido derivative of the alpha-amino acid complexed to copper, and this derivative precipitates from the aqueous solution. Preferred alpha-amino acids having a terminal amine are ornithine or lysine, and the resulting carbamido derivatives are citrulline or homocitrulline. In contrast to synthetic schemes of the prior art, which use reflux temperatures to react urea with ornithine, the method of this invention may be carried out at 30° C.-100° C., preferably 40° C.-80° C., more preferably 55° C.-65° C., and the reaction occurs within 0.5-5 hours, preferably 1-5 hours, more preferably 3-4.5 hours, although at 55° C.-60° C., the reaction preferably proceeds for at least 3.5 hours. Upon completion of the reaction, the precipitate may be recovered by filtration at ambient temperature, and the precipitate may be washed with water, preferably until blue color no longer appears in the filtrate.

This invention also provides an improved method of reducing ornithine contamination of citrulline by complexing citrulline with copper, and washing the precipitated citrulline:copper complex with water, whereby the ornithine:citrulline ratio in the precipitate is reduced. In the method of the invention, precipitated citrulline:copper complex is suspended in water and the pH of the suspension is adjusted with acid until the precipitate redissolves in water. The pH of the solution of citrulline:copper complex is adjusted with base to reprecipitate the citrulline:copper complex. Preferably, the aqueous suspension of precipitated citrulline:coper complex is acidified with hydrochloric acid, which brings citrulline into solution, and then base is added to reprecipitate a citrulline-copper complex. The reprecipitated citrulline:copper complex is recovered by filtration, and the recovered precipitate is washed with water until chloride no longer appears in the filtrate. Heat generated by the acidification and neutralization may be controlled by active cooling, preferably maintaining temperatures less than or equal to 45° C.

According to this invention, citrulline is recovered from a citrulline:copper complex by suspending the citrulline:copper complex in water; introducing hydrogen sulfide to dissolve the complex which produces an aqueous citrulline solution containing precipitated copper salts; and then removing precipitated copper salts from the solution by filtration. Hydrogen sulfide gas is added to the suspension in a sealed reaction vessel until no further consumption is observed. Consumption is monitored by observing the resultant pressure change. During the reaction the pH drops to below 4, preferably until pH ~3, while the temperature is maintained below ambient, preferably below 5° C. Temperature is then is elevated above ambient, preferably equal or greater than 30° C., to keep citrulline in solution during filtration to remove precipitated copper salts.

The invention provides further purification of the citrulline in solution recovered from the citrulline:copper complex. The recovered citrulline solution is neutralized, preferably by adjusting to pH=5.9±0.2, and treated with activated carbon, preferably by circulating the neutralized citrulline solution through an activated carbon adsorber bed. After activated carbon treatment, the citrulline solution is mixed with a water-miscible anti-solvent to precipitate citrulline from the aqueous solution. Suitable anti-solvents include 2-propanol, ethanol, methanol, or preferably acetone. The solvent/anti-solvent precipitation is carried out at low temperature, preferably 0° C.-10° C. All of the steps after recovery of the citrulline from the citrulline:copper complex are preferably carried out in a sealed vessel to minimize microbial contamination. The citrulline precipitate is dried to remove water and anti-solvent, and the resulting product is suitable for use in an injectable therapeutic composition.

DETAILED DESCRIPTION OF THE EMBODIMENTS

Details of various steps in the improved processes developed by the present inventors for producing pharmaceutical grade citrulline are discussed below.

Synthesis of Citrulline from Ornithine

The present inventors preserved the stereochemical structure around the alpha carbon of the alpha amino acid during reaction of amino groups elsewhere on the compound by complexing the alpha end of the molecule with a transition metal atom, as reported by Kurth 1938 and 1949. The initial production of the /-ornithine-copper complex is carried out as described by Kurtz. Kurtz describes a variety of transition metals as the complexing metal in the 1949 paper, but the preferred metal is copper (II), based on the ease of forming stable complexes and the ease with which copper (II) may subsequently be removed from the product. The copper is typically supplied as cupric sulfate, although complex formation from copper (II) acetate, cupric carbonate, or cupric oxide have also been reported.

Figure 2A:
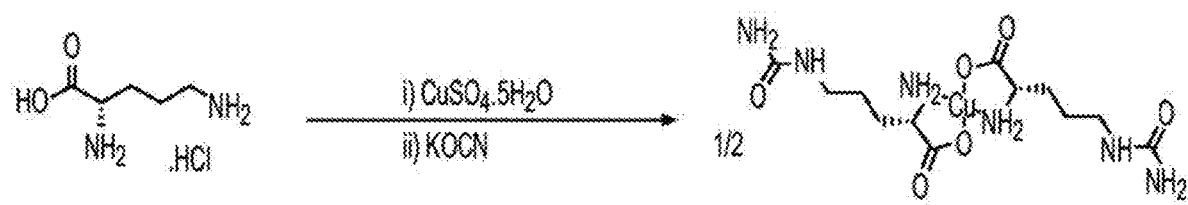
FIG. 2A shows the chemical structures of the reactants and products for the synthesis of citrulline from ornithine by reaction with cyanate.

The present inventors have discovered an alternative method of derivatizing the terminal amino group of the complexed alpha amino acid using cyanate rather than the urea reaction reported by Kurth. An example of this improved synthesis is shown in FIG. 2A and described in Example 3 below. Use of cyanate as the derivatizing agent has been found to produce fewer distinct product compounds, which simplifies purification of the desired citrulline product. Kurth carried out urea derivatization by refluxing the copper complex in the presence of excess urea. Cyanate derivatization may be carried out at lower temperatures (e.g. 55° C.-65° C.) which may contribute to higher yield of citrulline, based on the initial amount of ornithine. Cyanate is preferably provided in excess, and the reaction is driven by precipitation of the citrulline:copper complex. The precipitated complex is washed with water to remove unreacted copper (e.g., wash until no blue coloration persists in the filtrate). The precipitated copper complex of citrulline may be recovered and dried.

Enriching Citrulline as a Copper Complex

The inventors have discovered that the relative citrulline content of the reaction product(s) can be enhanced by reprecipitation of the citrulline:copper complex. Precipitated copper complex of citrulline (produced, for example, by reaction of a ornithine:copper complex with urea or cyanate in water) may be dried. The citrulline:copper complex may be redissolved by suspending the precipitate in water and acidifying the suspension until the complex dissolves. Acidification may be accomplished by adding concentrated acid, preferably hydrogen chloride, to the suspension while stirring. Once the copper: citrulline complex solution is clear, base (typically sodium hydroxide) is added to bring the pH up to 7-10. Both the acidification and subsequent neutralization steps are actively cooled (temperature not more than 45° C.) to protect the citrulline product from hydrolysis or reaction to produce side products. The precipitate is washed with water (e.g., until the filtrate is free of chloride by checking the filtrate for turbidity with silver nitrate), and then the precipitate is dried. Reprecipitation under these conditions is selective for citrulline:copper complex over ornithine:copper complex, because the ornithine complex is more soluble in water. If the dried complex contains higher than the desired level of ornithine contamination (e.g., greater than 10 mole % ornithine—as measured by NMR, for example), the complex may be redissolved and reprecipitated as necessary to further lower the relative amount of ornithine.

Recovering Citrulline from Its Copper Complex

Figure 2B:
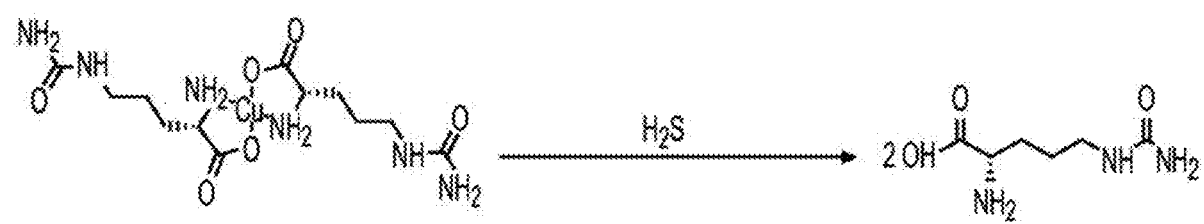
FIG. 2B shows the chemical structures for the citrulline:copper complex and the resultant citrulline when the complex is treated with hydrogen sulfide gas.

Once the ornithine content in the copper:citrulline complex precipitate is sufficiently low (preferably less than 10 mole % ornithine), the precipitate is resuspended in water and citrulline is freed from the complex by removing the copper as an inorganic precipitate, typically copper sulfide (See FIG. 2B). Sulfide may be introduced in a variety of salt forms, but the inventors have found it preferable to use hydrogen sulfide gas as the sulfide source. In a preferred mode, the aqueous suspension is placed in a stirred, pressure vessel. The air is then pumped out of the reactor's head space to form an under-pressure. The reactor is then repressurized with hydrogen sulfide gas over the aqueous suspension (preferably at low temperature, e.g., 0° C.-5° C., to maximize the solubility of hydrogen sulfide). Hydrogen sulfide is continuously added to the reactor to maintain parity with ambient pressure during consumption of this gas. Copper salts will precipitate, leaving citrulline in solution. As hydrogen sulfide is consumed, the pressure in the vessel decreases; the reaction is complete when the pressure stabilizes. Reaction of hydrogen sulfide with residual copper salts (for example chloride or sulfate) will lower the pH; typically the pH will be below 4, preferably pH~3. Copper salts typically include copper (II) sulfide, but may also include copper (I) sulfide and copper oxide. The solution temperature is elevated for filtration, typically to about 30° C., to promote solubility of the citrulline and drive off excess hydrogen sulfide gas, while precipitated copper salts are removed by filtration.

Purifying Citrulline

For pharmaceutical use, the active compound must be substantially free of contaminants, and further purification steps are necessary to produce a pharmaceutical grade product. For the purposes of this invention, substantially free of contaminants is considered to include: ornithine not more than (NMT) 0.8%, individual specified impurities NMT 0.15%, individual unspecified (unknown) impurities NMT 0.1%; total related substances NMT 1.3%, and Cu not more than 10 ppm. For citrulline manufactured from ornithine using copper complex to protect the alpha amino acid functions, the inventors have found that desired purification after citrulline is released from the copper complex can be achieved by activated carbon adsorption of contaminants and solvent/anti-solvent crystallization of the active pharmaceutical component.

The citrulline-containing aqueous solution remaining after removal of precipitated copper salts is neutralized to stabilize the citrulline against hydrolysis, to enhance adsorption of residual copper to activated carbon, and to facilitate solvent/anti-solvent precipitation of citrulline; pH is preferably adjusted to 5.9±0.2, the isoelectric point of citrulline. The neutralized citrulline solution may be passed through a nano-filter to remove any bacteria and/or bacterial cell wall fragments that contaminate the solution. The nano-filtered solution may be held in a semi-sterile reservoir for staging purposes between the subsequent purification steps. The neutralized citrulline solution is treated with activated carbon, either by mixing with carbon dust or passing the solution through an activated carbon adsorber bed. The aqueous citrulline-containing effluent from the activated carbon is mixed with an anti-solvent to induce anti-solvent crystallization. Suitable anti-solvents are miscible with water, including aliphatic alcohols, such as 2-propanol, ethanol or methanol, as well as acetone. A preferred anti-solvent for citrulline is acetone, when mixed with approximately two volumes of water (e.g., 1 volume of water to 1.8 volumes of acetone). Acetone is preferably pre-cooled so that the resultant suspension is 0° C.-10° C. The cooled suspension may be collected in a reservoir or processed by filtration immediately to recover the citrulline precipitate.

Microbial Control:

Because citrulline synthesis and purification occur in aqueous solution, there is increased risk of microbial contamination and endotoxin accumulation in the product. Washing the citrulline:copper precipitate, and addition of $H_2S$ to acid solution minimize any accumulation of microbes. From the exposure of the complex to $H_2S$ until treatment with acetone the aqueous solutions of citrulline are preferably kept in sealed vessels to limit microbial contamination and growth. Enclosing the purification steps to minimize contact with the environment and use of sterile filters to capture potential microbial contamination allows the manufacturing to be performed in an ISO 8 cleanroom. Alternatively, the final purification steps can be carried out in a sterile GMP environment of the sort used for aseptic filling of sterile dosage products (e.g., ISO Class 5/6).

If examination of the solution prior to the anti-solvent precipitation shows the amounts of microbes or endotoxin levels exceed those aceptable for injectable therapeutic compositions (e.g., 50 EU/g API, more preferably 20 EU/g), the product may be subjected to nano-filtration to remove microbes and endotoxin, before being recovered by anti-solvent precipitation and drying. The citrulline and water molecules pass through the nano-filtration membrane, but the larger bacteria and bacterial cell wall fragments are retained by the filter.

Filter Press

Figure 3:
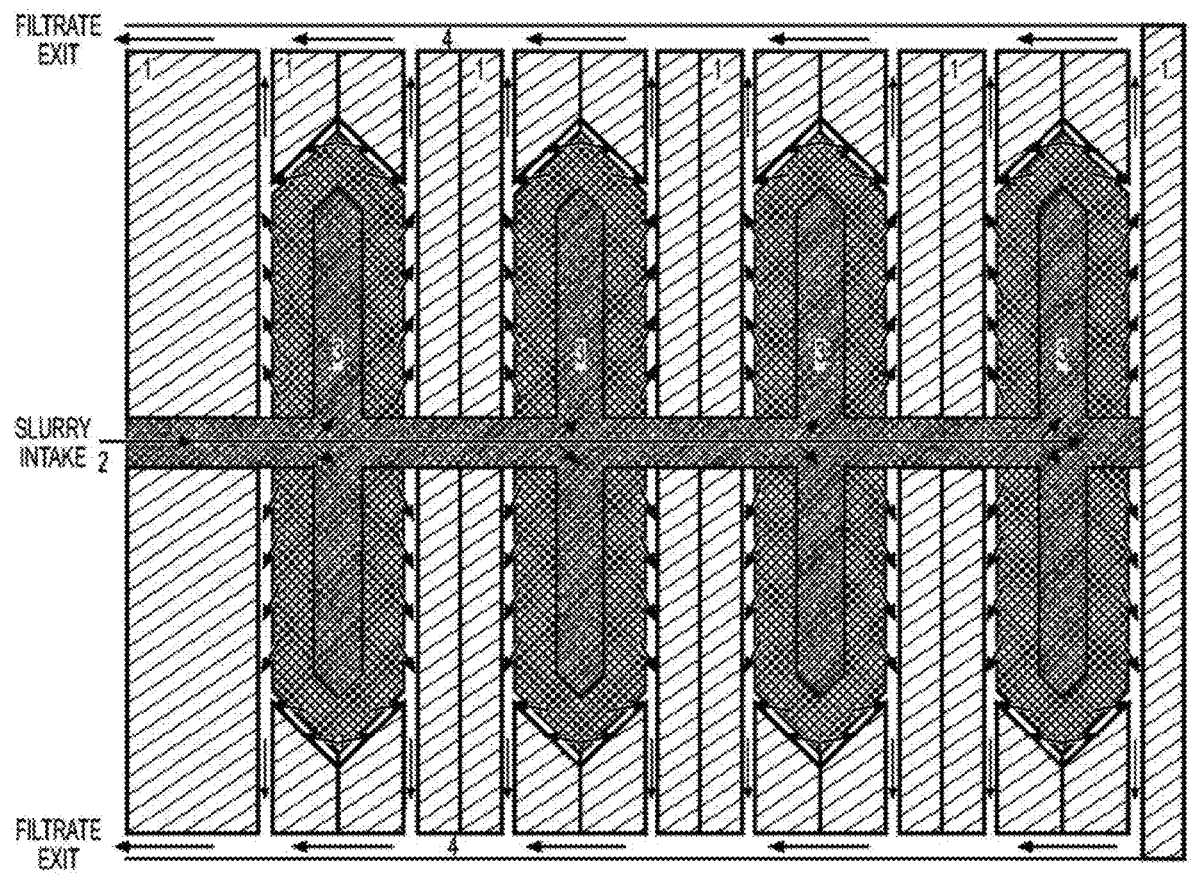
FIG. 3 shows a cross sectional depiction of a filter press.
Figure 4:
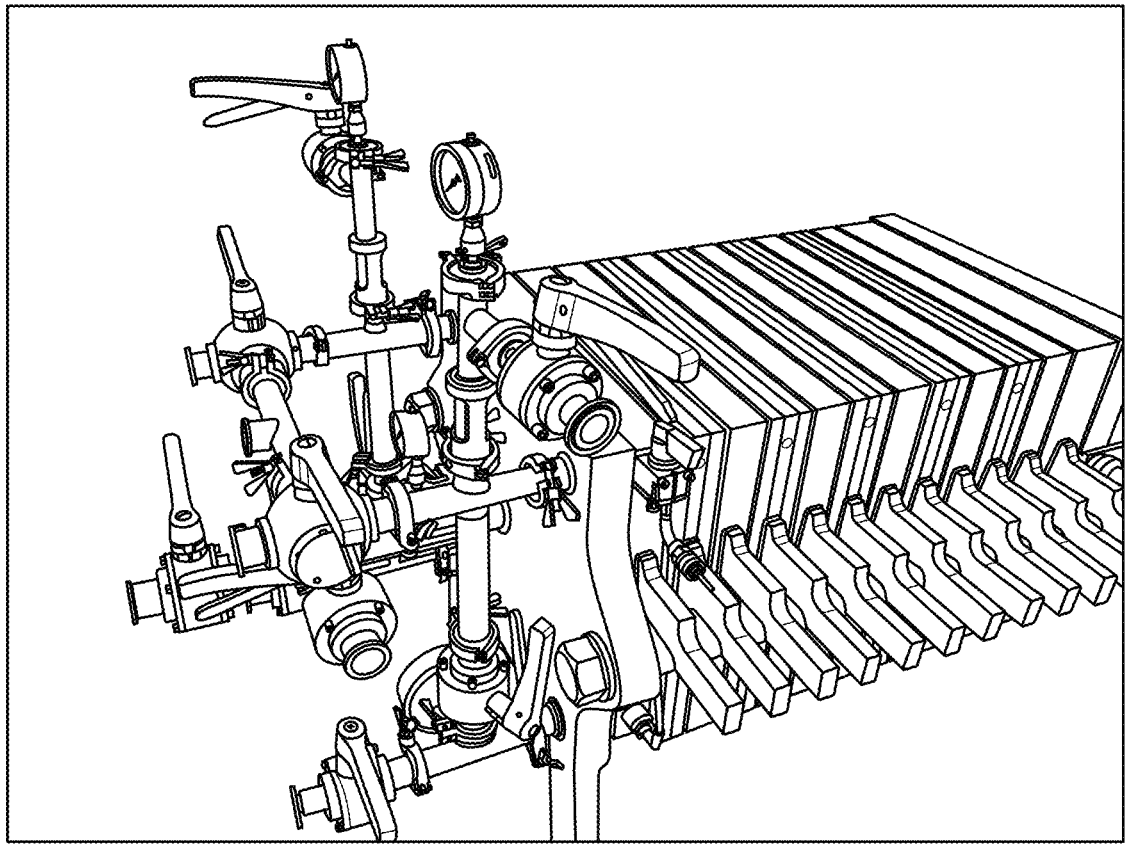
FIG. 4 shows a diagram of a filter press.

The reaction mixtures may be pumped through a filter press to collect/remove the suspended solids. See the general picture in FIG. 3, and the attached photograph in FIG. 4. The press is composed of a series of plates 1 which are then hydraulically pressed together. The hydraulic pressure ensures that the system is sealed. The suspension is then pumped through a central tube 2 where it spreads-out across several chambers 3 between the plates. The walls of the plates have a filter sheet, which allows the filtrate to flow past and exit via an internal cavity 4.

The general advantage of a filter press is that it allows a high surface area for filtration. This effect greatly accelerates the portion-wise collection and washing of the complex and API. This system may be used to collect the copper salts after exposure to hydrogen sulfide. In the latter case, the suspension is pumped from the reactor into the press, and the filtrate may then be passed through an in-line 5 µm filter to catch any residual particulate copper, then an in-line sterile 0.2 µm filter at the entry port of a semi-sterile container for holding.

The press may be used to collect:
Crude citrulline copper complex
The complex after the pH-driven re-precipitation
Precipitated copper salts (where citrulline leaves as solution in the filtrate)
Precipitated citrulline from anti-solvent precipitation prior to drying
Semi-Sterile Containers A useful semi-sterile container is basically a closed vessel equipped with a stirrer and ports for the addition and removal of liquid, and a pH meter. The container should be sterilized (e.g., treated with isopropyl alcohol solution and rinsed with water) directly prior to use and not opened during use. A sterile, air filter attached to the lid allows air to flow into the container as the liquid is being pumped out. The pH adjustment may be performed in this container, before treatment with activated carbon. The container is not particularly suitable for the long-term storage of the solutions.

Activated Carbon Adsorber Bed

The solution may be pumped from the semi sterile container through the activated carbon bed (a column packed with granulated activated carbon) pre-flushed with argon. The liquid is then returned to the semi-sterile container via an in-line 5 µm filter and the 0.2 µm sterile filter at the entry port. If the solution is pumped in a cyclic manner with the stirrer activated for not less than 6 hours, the sterile filter acts as a "microbial scrubber" continually collecting any microbes in the solution. The activated carbon primarily removes any organic impurities and will also remove any residual dissolved copper ions. The 5 µm filter catches any carbon particles which detach from the bed.

Sterile bags

After processing in the activated carbon adsorber bed, the solution may be passed into a single use sterile bag via another sterile filter. The solution may be stored longer in the bag than in the semi-sterile container. At this point, a test for the presence of microbes and/or bacterial endotoxins can be carried out. If endotoxins are observed, then the cut-off (nano-filtration) membrane may be employed. If not, the citrulline is ready to be recovered from the solution by anti-solvent precipitation. Collection of the solution in a sterile bag allows the citrulline solution to be processed batch-wise, where conveniently sized portions of citrulline are precipitated and recovered in the filter press.

Solvent/Anti-Solvent Mixing

The aqueous citrulline solution is mixed with pre-cooled anti-solvent to precipitate the citrulline from solution. After mixing with anti-solvent, the threat posed by bacterial growth is not higher than that for other APIs. The addition of the organic solvent makes the resulting solution bacteriostatic at a minimum. This precipitation improves the purity of citrulline, reducing, in particular, the ornithine levels, and allows for the rapid extraction of citrulline from solution.

Final Drying

The precipitate is dried to remove residual acetone and water. Drying may be carried-out in a conical dryer, firstly to drive off the acetone anti-solvent, then moisture and finally the water of crystallization. The conical dryer can also be used to homogenize the product. The final, dry product of anti-solvent precipitation may be stored, and ultimately dissolved in sterile aqueous diluent for therapeutic administration.

On dissolution in sterile aqueous media, citrulline prepared as described herein may be used to treat pulmonary hypertension (WO/2000/073322), bronchopulmonary dysplasia (WO/2009/099998), sickle cell crisis (WO/2018/157137), cardiac surgery patients (WO/2005/082042), cardiopulmonary bypass patients (WO/2018/125999), and vasospasm as a complication of subarachnoid hemorrhage (WO/2009/099999), by parenteral administration as described in these documents, incorporated herein by reference.

EXAMPLES

Example 1

Synthesis of Citrulline from Ornithine Using Urea

Figure 1A:
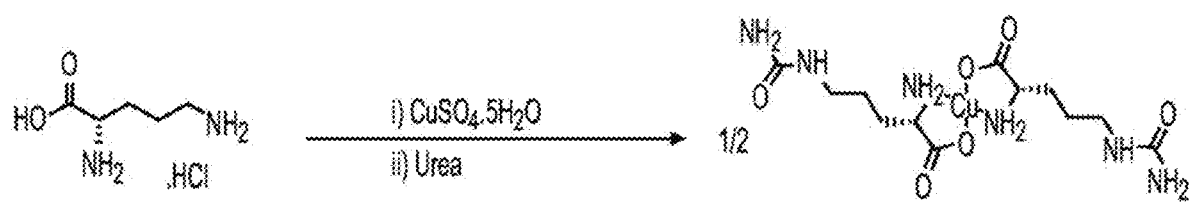
FIG. 1A shows the chemical structures of the reactants and products for the synthesis of citrulline from ornithine by reaction with urea.

L-Citrulline is synthesized from L-ornithine and urea. A flow chart of the reaction is shown in FIG. 1A.

L-Citrulline is prepared synthetically starting from L-ornithine hydrochloride. Into a 120-L reactor containing approximately 50 liters of water, 10 kilograms of L-ornithine hydrochloride is added and dissolved. The solution is neutralized with potassium hydroxide and then converted to its copper complex by the addition of 15 kg copper sulfate (molar equivalent amount). The copper complex protects the 2-amino carboxylic acid functionality in the molecule while chemistry is performed on the terminal amino group. The L-ornithine copper complex is then exposed to an excess of urea at reflux, which promotes its conversion to the copper complex of L-citrulline. The resulting copper complex of L-citrulline then is precipitated and collected by filtration.

The isolated copper complex of L-citrulline is dried and testing is performed. The appearance is verified, and an in-use performance test is done to determine suitability to proceed.

Example 2

Purification of Citrulline from Copper-Citrulline Complex

Figure 1B:
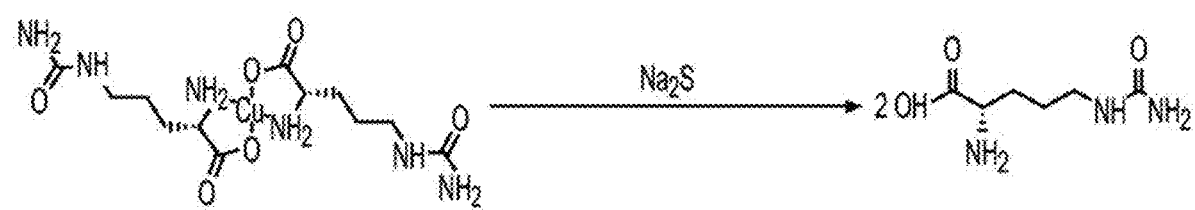
FIG. 1B shows the chemical structures for the citrulline:copper complex and the resultant citrulline when the complex is treated with inorganic sulfide.

L-Citrulline synthesized from L-ornithine and urea is purified by resin-based purification and recrystallization. A flow chart of the reaction is shown in FIG. 1B.

In a 120-L reactor, ~13 kilograms of the L-citrulline copper complex prepared in Example 1 is added to a stirring solution of sodium sulfide ($Na_2S$) in water (approximately 8 kilograms $Na_2S$ in 50 liters of water), causing the precipitation of copper sulfide and the freeing of L-citrulline. The solution is filtered to remove the copper salts. The pH of the resulting aqueous solution containing the sodium salt of L-citrulline and residual sodium sulfide is lowered to 4 by the addition of an acidic ion exchange resin (such as Amberlite™). A constant stream of argon gas is passed through the solution to remove the residual sulfide as hydrogen disulfide. The pH of the solution is then raised to 5.9±0.2 using sodium hydroxide to form isoelectric L-citrulline.

Activated carbon is then added to the reaction mixture to remove residual impurities, in particular residual copper ions. The solids (Amberlite™ and activated carbon) are then removed by filtration, and the filtrate is concentrated to approximately 50 liters (either by evaporation or reverse osmosis). L-citrulline is then precipitated from the aqueous solution by the addition of an equal part of acetone, and the mixture is cooled to near 0° C. The precipitate is collected by filtration and dried in a vacuum oven.

The non-sterile bulk powder is then reconstituted and processed for endotoxin reduction and sterile filtration steps followed by crystallization, drying and micronization in an aseptic environment. The sterile bulk powder is then used as the "raw material" for aseptic filling into glass vials to produce the finished drug product which may be reconstituted with a sterile diluent prior to use.

Example 3

Synthesis of Citrulline from Ornithine Using Cyanate

L-Citrulline was prepared synthetically starting from L-ornithine hydrochloride. Into a reactor containing sodium hydroxide (11 kg) in water (170 kg), L-ornithine hydrochloride (44 kg) was added and dissolved. The temperature was maintained at no more than 40° C. by active cooling. The ornithine was then converted to its copper complex by the addition of 0.5 molar equivalents of copper sulfate (33 kg) and stirring at ambient temperature for more than 15 minutes. The copper complex protects the 2-amino carboxylic acid functionality of the molecule while chemistry is performed on the terminal amino group. A molar excess of potassium cyanate (32 kg) is then added to the L-ornithine copper complex, and the solution is held at 55° C.-65° C. for 4.0-4.5 hours, which promotes its conversion to the copper complex of L-citrulline. The resulting copper complex of L-citrulline precipitates during the reaction, and it is collected by filtration.

Example 4

Purification of Therapeutic Grade Citrulline

The dry copper:citrulline complex produced in Example 3 is added to a reactor containing water, which is stirred to resuspend the complex. Concentrated hydrogen chloride solution is added to convert the complex into a solution of copper (II) chloride and citrulline hydrochloride, while the temperature of the reactor is maintained at no more than 45° C. by active cooling. Once the contents of the reactor are in solution, sodium hydroxide is added to raise the pH to 7-10, while the temperature is maintained at no more than 40° C. The copper complex of citrulline then precipitates. The precipitate is collected and washed with water until no blue coloration persists in the filtrate.

The washed precipitate is tested to determine the relative ornithine content. If ornithine is greater than 10 mole %, the precipitate is redissolved and resuspended as described above, until the ornithine content is lowered to not more than 10 mole %.

Once the precipitate achieves the desired ornithine content, it is resuspended in water in a stirred reactor, and hydrogen sulfide gas is introduced into the suspension to precipitate copper sulfide and dissolve citrulline. The solution is warmed to 30° C. ±2° C. to ensure citrulline is fully solubilized, and precipitated copper salts are removed by filtration. The citrulline-containing filtrate is passed thorough micro- and sterile-filtrations and collected in a semi-sterile reactor.

Activated carbon is used to remove residual impurities, in particular an organic component and residual copper ions. The pH of the resulting aqueous solution containing L-citrulline and residual copper is adjusted to 5.9 ±0.2 with sodium hydroxide to form isoelectric citrulline solution. The isoelectric citrulline solution is treated with active carbon granules, preferably by passing the solution through an active carbon adsorber bed, and passed through micro and sterile filters after the active carbon treatment.

L-citrulline is then precipitated from the aqueous solution by the addition of acetone anti-solvent, and the mixture is cooled to near 0° C. Addition of 1.5 to 2 volume equivalents of acetone produce dihydrate crystals of citrulline. The precipitate is collected by filtration. The crystals are dried in a vacuum in a conical dryer at temperature of no more than 45° C. to remove acetone and water, resulting in an anhydrous crystalline solid. This solid citrulline corresponds to the orthorhombic δ form anhydrous crystals reported by Allouchi, et al., 2014 (Cryst. Growth Des., 14:1279-1286).

Either the dihydrate crystals or the anhydrous crystals may be used therapeutically. The solid or an aqueous solution/suspension may be administered enterally, or the solid may be redissolved for parenteral administration. To produce a final therapeutic product, the non-sterile bulk powder was reconstituted and underwent endotoxin reduction and sterile filtration steps followed by crystallization, drying and micronization in an aseptic environment. The sterile bulk powder was then used as the "raw material" for aseptic filling into glass vials to produce the finished drug product which was reconstituted with a sterile diluent prior to use.

The invention claimed is:

1. A method of adding a terminal carbamido group to an alpha amino acid comprising:
    (a) obtaining an alpha-amino acid having a terminal amine complexed with copper in aqueous solution;
    (b) reacting the alpha amino acid having a terminal amine with a cyanate; and
    (c) recovering a carbamido derivative of the alpha-amino acid complexed to copper as a precipitate.

2. The method of claim 1, wherein the alpha-amino acid having a terminal amine is at least one member selected from the group consisting of ornithine or lysine, and/or wherein the carbamido derivative of the alpha-amino acid is at least one member selected from the group consisting of citrulline or homocitrulline.

3. The method of claim 1, wherein temperature of step (b) is between 30° C. and 100° C., and/or the time of reaction is between 0.5 and 5 hours.

4. The method of claim 1, wherein step (b) results in a reaction mixture that is cooled to at least ambient temperature or lower prior to step (c) and/or wherein the precipitate recovered in step (c) is washed with water until a blue color no longer appears.

* * * * *